(12) United States Patent
Zhu et al.

(10) Patent No.: US 10,821,309 B2
(45) Date of Patent: Nov. 3, 2020

(54) HARNESS DESIGN FOR RESPIRATORY SYSTEM

(71) Applicant: Honeywell International Inc., Morris Plains, NJ (US)

(72) Inventors: Jie Zhu, Shanghai (CN); Gio Xu, Shanghai (CN); Bruce Liu, Shanghai (CN); Zhao Xia Jin, Shanghai (CN)

(73) Assignee: Honeywell International Inc., Morris Plains, NJ (US)

( * ) Notice: Subject to any disclaimer, the term of this patent is extended or adjusted under 35 U.S.C. 154(b) by 244 days.

(21) Appl. No.: 15/669,348

(22) Filed: Aug. 4, 2017

(65) Prior Publication Data

US 2019/0030378 A1    Jan. 31, 2019

(30) Foreign Application Priority Data

Jul. 31, 2017   (CN) .......................... 2017 1 0638365

(51) Int. Cl.
*A62B 9/04* (2006.01)
*A62B 7/02* (2006.01)
(Continued)

(52) U.S. Cl.
CPC ................. *A62B 9/04* (2013.01); *A45F 3/14* (2013.01); *A62B 7/02* (2013.01); *A62B 25/00* (2013.01);
(Continued)

(58) Field of Classification Search
CPC .................. A45F 3/14; A45F 2003/146; A45F 2003/142; A45F 3/04; A45F 3/02;
(Continued)

(56) References Cited

U.S. PATENT DOCUMENTS

| | | | |
|---|---|---|---|
| 2,224,568 A | 12/1940 | Altorfer | |
| 4,099,656 A * | 7/1978 | Neumann | ................ A45C 3/00 294/157 |

(Continued)

FOREIGN PATENT DOCUMENTS

| | | |
|---|---|---|
| CA | 996517 | 9/1976 |
| FR | 2343443 A1 | 10/1977 |
| WO | 96/28065 A1 | 9/1996 |

OTHER PUBLICATIONS

Europe Patent Application No. 17184827.8, Extended European Search Report, dated Feb. 1, 2018, 10 pages.

(Continued)

*Primary Examiner* — Victoria Murphy
(74) *Attorney, Agent, or Firm* — Alston & Bird LLP

(57) ABSTRACT

A harness may be used to carry a breathable air system. Generally, the harness may comprise at least one shoulder strap and a plurality of attachments configured to attach the at least one shoulder strap to the breathable air system. Additionally, the plurality of attachments may allow the breathable air system to be configured into a plurality of strap configurations. For example, the plurality of strap configurations may include a hip configuration, a waist configuration, a leg configuration, and/or a back configuration. In some configurations, an additional/accessory strap may be used to more securely carry the breathable air system in the plurality of strap configurations.

8 Claims, 10 Drawing Sheets

(51) Int. Cl.
    *A45F 3/14*     (2006.01)
    *A62B 25/00*     (2006.01)
    *A45F 3/02*     (2006.01)
    *A45F 3/04*     (2006.01)
    *B63C 11/02*     (2006.01)

(52) U.S. Cl.
    CPC . *A45F 3/02* (2013.01); *A45F 3/04* (2013.01); *A45F 2003/142* (2013.01); *A45F 2003/146* (2013.01); *A61M 2202/0208* (2013.01); *A61M 2209/088* (2013.01); *B63C 2011/026* (2013.01)

(58) Field of Classification Search
    CPC ......... A45F 2003/025; B63C 2011/026; A62B 25/00; A41D 2400/48; A41D 2400/482; A61F 5/37; A61F 5/373; A61F 5/3746; A61F 5/3738; A61F 5/3761
    See application file for complete search history.

(56) References Cited

U.S. PATENT DOCUMENTS

| | | | |
|---|---|---|---|
| 4,810,102 A * | 3/1989 | Norton | A45C 1/04 |
| | | | 150/108 |
| 5,400,934 A * | 3/1995 | Ducros | A45F 3/04 |
| | | | 128/202.15 |
| 6,003,744 A | 12/1999 | Culjak | |
| 6,220,493 B1 | 4/2001 | Iijima et al. | |
| 6,460,746 B1 | 10/2002 | Amram | |
| 9,009,931 B2 | 4/2015 | Jensen | |
| 2003/0154981 A1 | 8/2003 | Spruiell | |
| 2004/0082238 A1* | 4/2004 | Jacoway | B63C 11/02 |
| | | | 441/136 |
| 2005/0011520 A1 | 1/2005 | Rowe | |
| 2008/0277434 A1 | 11/2008 | Sacks | |
| 2013/0292441 A1 | 11/2013 | Shen | |
| 2016/0100673 A1 | 4/2016 | Demskey | |
| 2017/0119106 A1* | 5/2017 | Leslie | A01K 27/005 |

OTHER PUBLICATIONS

Annex to the communication dated Jan. 20, 2020 for EP Application No. 17184827, 4 pages.
Annex to the communication dated Jun. 15, 2020 for EP Application No. 17184827, 9 pages.
Invitation to Indicate the Basis for Amendments received for EP Application No. 17184827.8, dated Jan. 20, 2020, 1 page.
Office Action received for European Application No. 17184827.8, dated May 23, 2019, 8 pages.
Summons to Attend Oral Proceeding received for EP Application No. 17184827.8, Jun. 15, 2020, 2 pages.

* cited by examiner

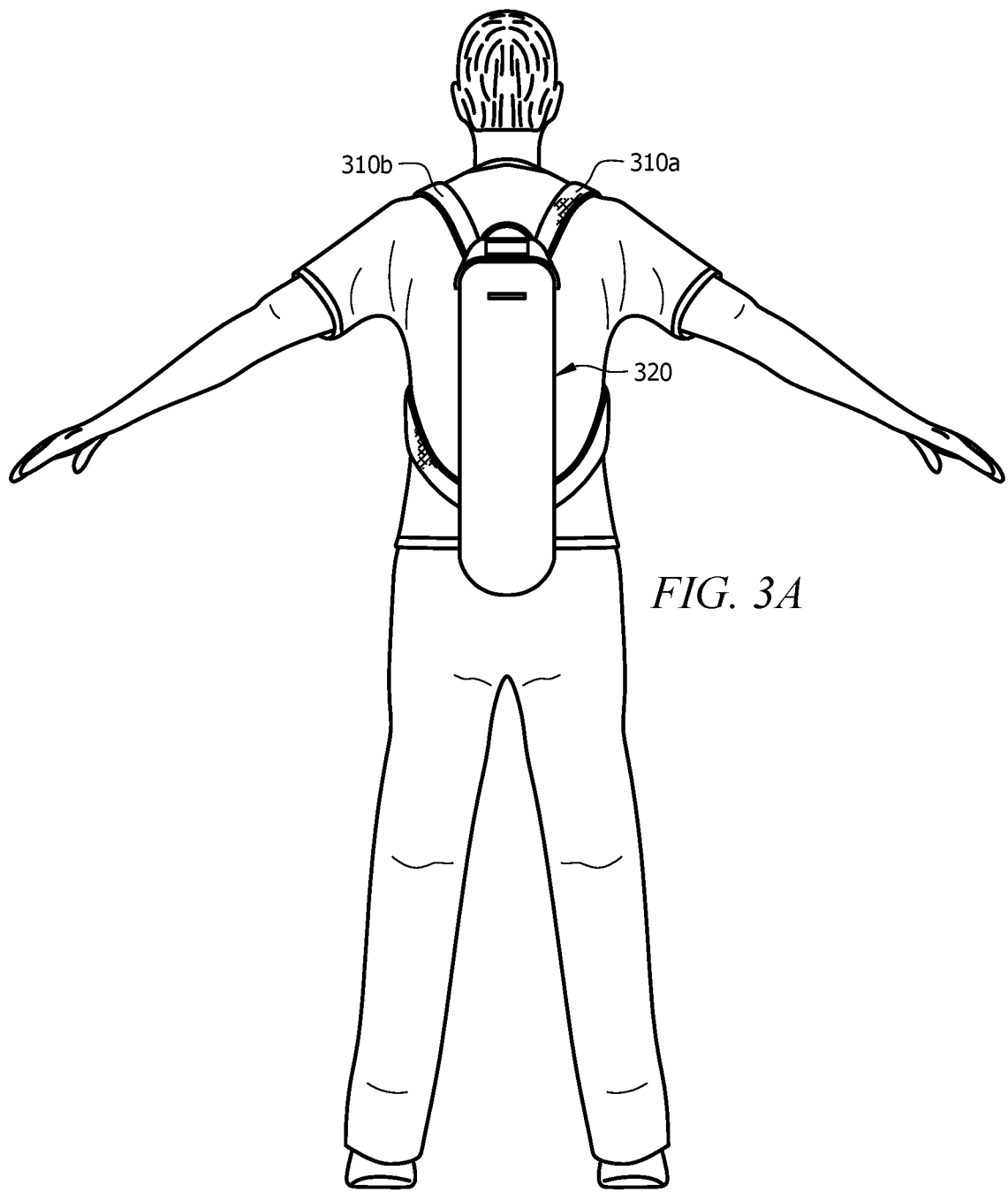

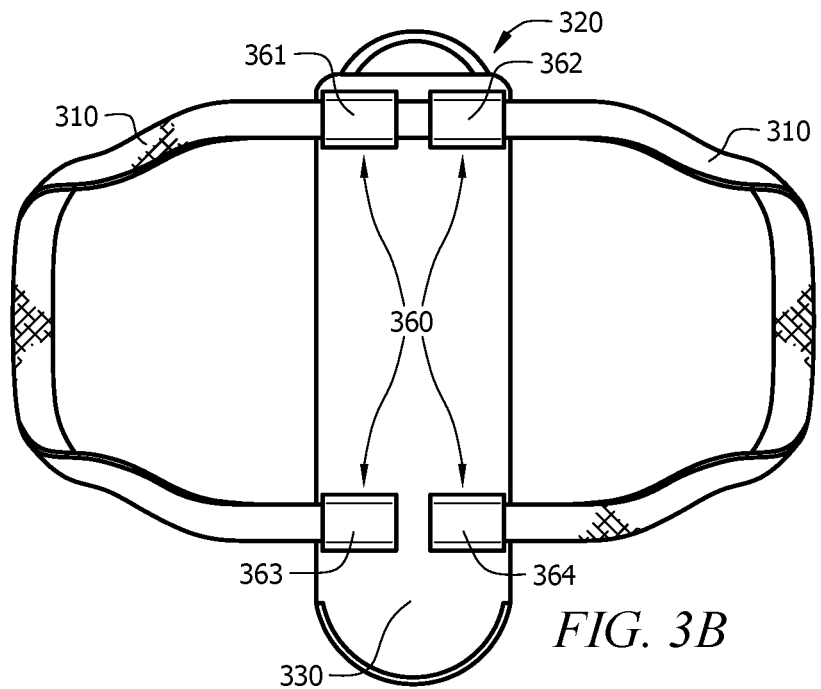
*FIG. 3B*
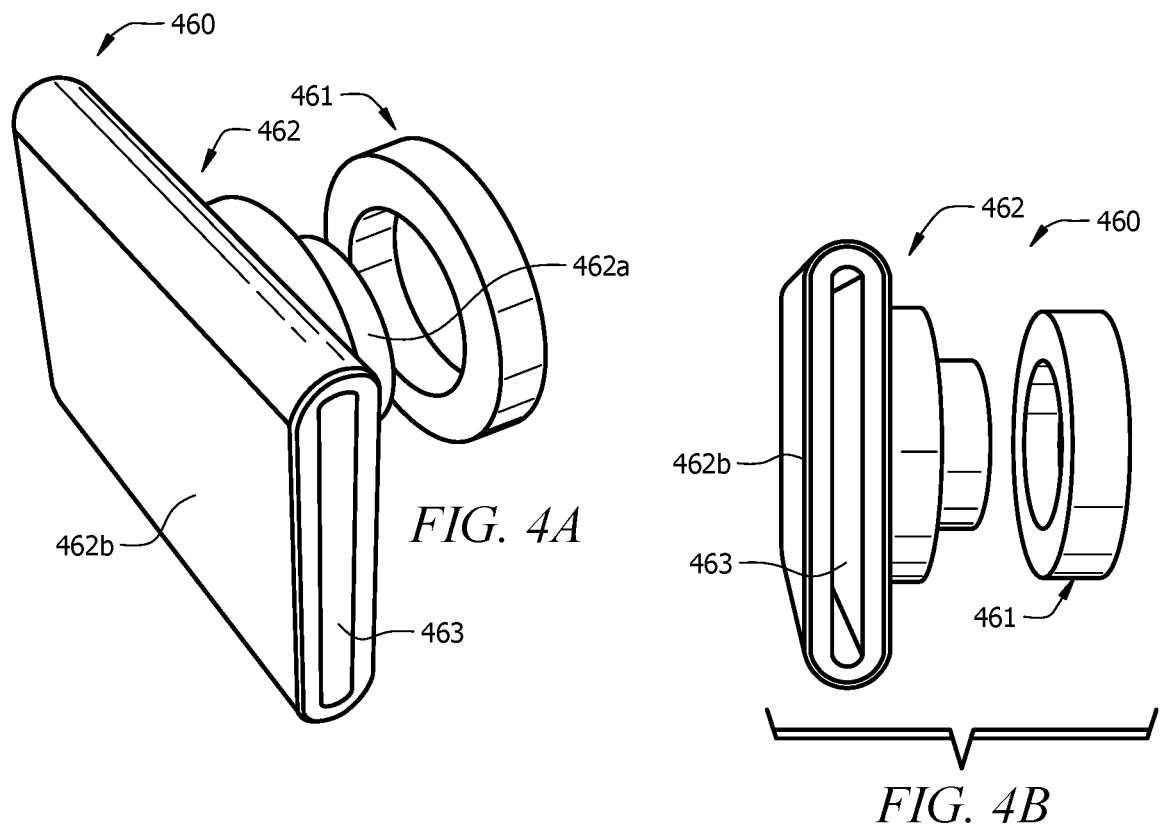
*FIG. 4A*
*FIG. 4B*

HARNESS DESIGN FOR RESPIRATORY SYSTEM

CROSS-REFERENCE TO RELATED APPLICATIONS

This application claims priority to China Patent Application No. 201710638365.0 (entitled HARNESS DESIGN FOR RESPIRATORY SYSTEM, filed Jul. 31, 2017), which is incorporated herein by reference.

STATEMENT REGARDING FEDERALLY SPONSORED RESEARCH OR DEVELOPMENT

Not applicable.

REFERENCE TO A MICROFICHE APPENDIX

Not applicable.

BACKGROUND

Respiratory equipment may be used in various environments and working scenarios/tasks. For example, within industry, some work environments may contain insufficient oxygen or harmful dusts, fogs, smokes, mists, fumes, gases, vapors, or sprays requiring workers to use respiratory equipment. The use of respiratory equipment in harmful environments may be imperative in preventing diseases, lung impairment, and/or death. Therefore, industry standards may require a user to wear respiratory equipment while working in various environments and situations. Often times, respiratory equipment may comprise a cylinder containing breathable oxygen for the user. In working situations, the user may need to carry the cylinder containing breathable oxygen for long periods of time and/or while accomplishing difficult tasks such as climbing a ladder. Due to differences in work environments and tasks, inventors have found that an interchangeable harness design may be helpful to increase the user's comfort, stability, range of motion, safety, etc.

BRIEF DESCRIPTION OF THE DRAWINGS

For a more complete understanding of the present disclosure, reference is now made to the following brief description, taken in connection with the accompanying drawings and detailed description, wherein like reference numerals represent like parts.

FIG. 3A illustrates a back view of a user wearing an exemplary embodiment of a breathable air system in a back configuration using two shoulder straps;

FIG. 3B illustrates a back view of an exemplary embodiment of a breathable air system configured for interaction with a user's back and comprising two shoulder straps (similar to the exemplary embodiment shown in FIG. 3A);

FIG. 4A illustrates a perspective view of a rotatable strap holder comprising a first portion and a second portion;

FIG. 4B illustrates a side view of an exemplary embodiment of a rotatable strap holder comprising a first portion and a second portion;

DETAILED DESCRIPTION

Figure 1A:
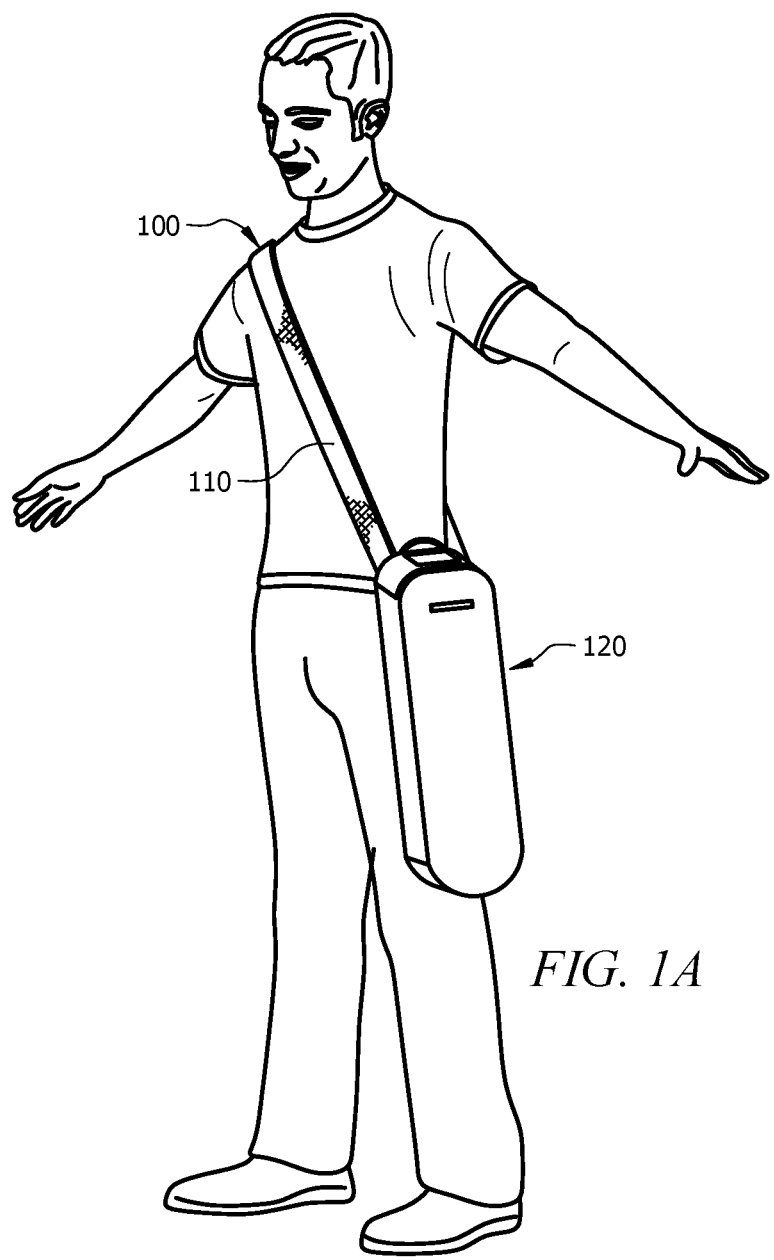
FIG. 1A illustrates a perspective view of a user wearing an exemplary embodiment of a breathable air system in a hip configuration using a shoulder strap.

It should be understood at the outset that although illustrative implementations of one or more embodiments are illustrated below, the disclosed systems and methods may be implemented using any number of techniques, whether currently known or not yet in existence. The disclosure should in no way be limited to the illustrative implementations, drawings, and techniques illustrated below, but may be modified within the scope of the appended claims along with their full scope of equivalents.

The following brief definition of terms shall apply throughout the application:

The term "comprising" means including but not limited to, and should be interpreted in the manner it is typically used in the patent context;

The phrases "in one embodiment," "according to one embodiment," and the like generally mean that the particular feature, structure, or characteristic following the phrase may be included in at least one embodiment of the present invention, and may be included in more than one embodiment of the present invention (importantly, such phrases do not necessarily refer to the same embodiment);

If the specification describes something as "exemplary" or an "example," it should be understood that refers to a non-exclusive example;

The terms "about" or "approximately" or the like, when used with a number, may mean that specific number, or alternatively, a range in proximity to the specific number, as understood by persons of skill in the art field (for example, +/−10%); and If the specification states a component or feature "may," "can," "could," "should," "would," "preferably," "possibly," "typically," "optionally," "for example," "often," or "might" (or other such language) be included or have a characteristic, that particular component or feature is not required to be included or to have the characteristic. Such component or feature may be optionally included in some embodiments, or it may be excluded.

The embodiments of this disclosure typically relate to respiratory equipment, and, more specifically, to respiratory equipment which employ a harness. Typically, respiratory equipment may be used in various environments and working scenarios/tasks. For example, within industry, some work environments may contain insufficient oxygen or harmful dusts, fogs, smokes, mists, fumes, gases, vapors, or sprays requiring workers to use respiratory equipment. The use of respiratory equipment in harmful environments may be imperative in preventing diseases, lung impairment, and/or death. Therefore, industry standards may require a user to wear respiratory equipment while working in various environments and situations. Often times, respiratory equipment may comprise a cylinder containing breathable oxygen for the user. In working situations, the user may need to carry the cylinder containing breathable oxygen for long periods of time and/or while accomplishing difficult tasks such as climbing a ladder. Due to differences in work environments and tasks, an interchangeable harness design may be helpful to increase the user's comfort, stability, range of motion, safety, etc. Interchangeable harness designs may focus on allowing the user to switch between various configurations such as wearing the respiratory equipment on his/her back, waist, hip, leg, etc. Generally, conventional embodiments may focus on one method of wearing the respiratory equipment/breathable air system. This may force the user to buy multiple types of carrying gear/harnesses for the breathable air system and/or may force the user to adapt one method of carrying the breathable air system regardless of comfort level or constraints within the work environment. In contrast, disclosed embodiments provide more flexibility with regards to wearing configuration for respiratory equipment utilizing a cylinder.

Disclosed embodiments comprise a harness design which allows the user to wear a breathable air system in multiple configurations. For example, the user may wear the breathable air system on his/her shoulder, waist, hip, back, leg, or combinations thereof. Additionally, disclosed embodiments may allow for interchangeability between the various configurations depending on the user's preference and/or work scenario/environment. For example, when the user needs to climb a ladder, space may be very limited at the front of the user's body, so the user may need to shift the breathable air system to the side or to the back. In another example, when the user does not have space to the sides of his/her body due to a confined work environment, the user may shift the breathable air system to his/her back or waist. In another example, the user may be required to sit, for example on a rescue boat or cart, causing the user to shift the breathable air system to his/her back similar to a backpack wearing style. Thus, embodiments of this disclosure may provide such a universally adaptable harness for carrying/wearing a breathable air system.

In an exemplary embodiment, the harness may comprise at least one shoulder strap (an typically only a single shoulder strap, for example as shown in FIG. 1A-FIG. 9B) and a plurality of attachments (e.g. attachment mechanisms) configured to attach the at least one shoulder strap to the breathable air system (and typically, embodiments would also include a sleeve or housing configured to hold such breathable air systems, with the strap and attachments attaching/connecting thereto). Additionally, the plurality of attachments may be used to configure the at least one shoulder strap into a plurality of strap configurations (typically with either one or two strap portions for wearing on a user's body). In some embodiments, the plurality of strap configurations may include a hip configuration, a waist configuration, and/or a back configuration. Typically, within a hip configuration, the strap may be oriented to interact with the user's shoulder in, for example, a messenger bag style. Typically, within a waist configuration, the strap may be oriented in a similar manner to the hip configuration; however, the breathable air system may be tilted to span across the user's waist (thereby shifting the weight of the breathable air system more evenly across the front of the user's body). Typically, within a back configuration, the strap may be oriented to interact with both of the user's shoulder, for example, in a backpack style. Typically, embodiments would allow the harness to be worn in at least two (and often at least three) such configurations.

In some embodiments, the plurality of attachments (e.g. attachment mechanisms) may comprise one or more rotatable strap holder. More typically, two or more of at least four rotatable strap holders would be used. The rotatable strap holders may allow the at least one shoulder strap to slide back and forth (within the strap holder), and all of the rotatable strap holders typically rotate at least 90 and typically 360 degrees. So, for example, two of the four or more of the rotatable strap holders may serve as end points for the strap (e.g. allowing rotation but not allowing the strap to slide within the end point rotatable strap holders), while two of the rotatable strap holders would allow both rotation (e.g. at least 90 degrees, but typically between 180 degrees to 360 degrees) and sliding of the strap within the strap holders to adjust the length of various segments/portions of the strap. Typically, the two rotatable strap holders on the bottom of the breathable air system would not allow sliding of the strap (e.g. serve as end points), while the two holders on top would allow sliding. Typically, the rotatable strap holder may have a first portion and a second portion. The first portion of the rotatable strap holder may be configured to attach to a back plate of the breathable air system. The second portion of the rotatable strap holder may be configured to interact with the at least one shoulder strap in a sliding manner. Typically, the second portion of the rotatable strap holder may comprise an aperture/opening to allow insertion of the at least one shoulder strap therethrough. In this manner, during use, the at least one shoulder strap may slide back and forth through the aperture/opening (for example, to adjust the length of the various portion of the strap with regards to the various rotatable strap holders). In some embodiments, the first portion of the rotatable strap holder may detach from the second portion of the rotatable strap holder. In some embodiments, the first portion of the rotatable strap holder may be permanently affixed to the second portion of the rotatable strap holder. In this disclosure, "permanently affixed" means that the user would have a difficult time removing the two portions and/or may cause the rotatable strap holder to break and/or be damaged by trying to separate the two portions. In some embodiments, the plurality of attachments may comprise buckles, hooks, D-rings, carabiners, metal-head buckles, or other attachment mechanisms which allow for easy and secure attachment.

In some embodiments, the at least one shoulder strap may comprise a pad configured to interact with the user's shoulders, waist, and/or back (depending on the configuration the user chooses). Typically, the at least one shoulder strap may comprise one or more attachments configured to interact with other attachments located on the harness. Generally, at least one attachment may be located on a first end of the pad and at least one attachment may be located on a second end of the pad. Additionally, the at least one shoulder strap may comprise a length adjustment mechanism, for example to better fit varying body types/sizes (e.g. allowing the user to adjust/alter the length of the strap to be longer or shorter within a pre-determined range of lengths). In some embodiments, the length adjustment mechanism may comprise one or more strap adjusters, strap loops, and/or clasp buckles.

In some embodiments, the harness may comprise an additional/accessory strap. Typically, the additional/accessory strap may be configured to interact with the user's hip and/or leg to provide a more secure attachment of the breathable air system to the user's body. Typically, the additional/accessory strap may attach to at least one attachment located on the lower half of the breathable air system and/or may attach to at least one attachment located on the at least one shoulder strap (depending on the configuration). For example, the back plate of the breathable air system may interface with the user's leg and the additional/accessory strap may be wrapped around the user's leg to provide additional support of the breathable air system (for example, in hip/leg configuration). In some embodiments, the additional/accessory strap may interact with one or more attachments located on the at least one shoulder strap. This may allow the user to configure the breathable air system to be worn on his/her waist or back (for example, like a messenger bag). While persons of skill should understand the disclosed embodiments based on the above disclosure, the following figures may provide specific examples that may further clarify the disclosure.

Turning now to the drawings, FIG. 1A-FIG. 3B illustrate an exemplary embodiment in various configurations. FIG. 1A illustrates a perspective view of a user wearing an exemplary embodiment of a breathable air system 120 in a hip configuration using a harness 100 comprising a shoulder strap 110. In some embodiments, the breathable air system 120 on the harness 100 might include a housing or sleeve configured to hold (typically removably) on air/oxygen cylinder, although in other embodiments, the shoulder strap 110 might directly connect/attach to the cylinder itself (e.g. with rotatable strap holders (shown in FIG. 1B) directly mounted to the cylinder). The user is shown to be wearing the breathable air system 120 in a messenger bag style. In other words, the back plate of the breathable air system 120 interfaces with the side of the user's body (e.g. hip and/or leg). Additionally, the user is shown to be wearing the breathable air system 120 on the left side of his body. The user could also wear the breathable air system 120 in a similar manner on the right side of his body. In some embodiments, the user may align the shoulder strap 110 and the breathable air system 120 on the same side of the body. For example, the shoulder strap 110 may interact with the user's right shoulder, and the breathable air system 120 may interface with the user's right side of the body. For example, the shoulder strap 110 may interact with the user's left shoulder, and the breathable air system 120 may interface with the user's left side of the body. In FIG. 1A, the breathable air system 120 (e.g. housing) comprises an outer casing, a mounting back plate (shown in FIG. 1B), and/or, in some embodiments, may additionally comprise accessories such as a hose.

Figure 1B:
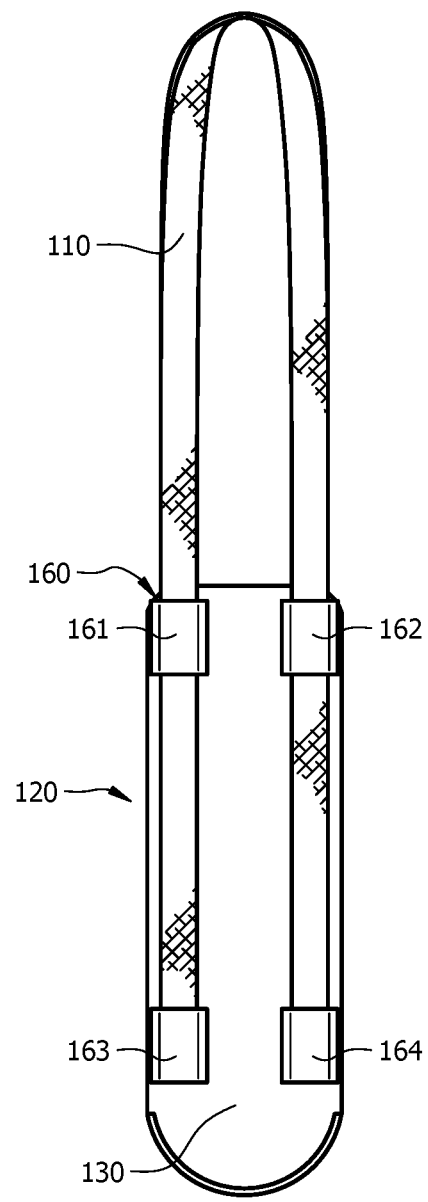
FIG. 1B illustrates a back view of an exemplary embodiment of a breathable air system configured for interaction with a user's hip and comprising a shoulder strap (similar to the exemplary embodiment shown in FIG. 1A)

FIG. 1B illustrates a back view of an exemplary embodiment of a breathable air system 120 configured for interaction with a user's hip and comprising a shoulder strap 110 (similar to the exemplary embodiment shown in FIG. 1A), and shows how to configure the strap accordingly using the rotatable strap holders 161, 162, 163, 164. In the exemplary embodiment of FIG. 1B, two attachments 161, 162 are shown to be located on the upper/top half of the back plate 130 closest to the top of the breathable air system 120, and two attachments 163, 164 are shown to be located on the lower/bottom half of the back plate 130 closest to the bottom of the breathable air system 120. However, in some embodiments, the number and location of attachments 161, 162, 163, 164 may vary. The attachments 161, 162, 163, 164 in FIG. 1B comprise rotatable strap holders 160 which may allow the shoulder strap 110 to slide back and forth and rotate 360 degrees. In the exemplary embodiment of FIG. 1B, the shoulder strap 110 is shown to be pulled upward through the two attachments 161, 162 located on the upper/top half of the back plate 130 (with attachments 163, 164 facing end points on the bottom of the back plate), thereby forming a loop above the breathable air system 120 for interaction with the user's shoulders. So, in the configuration of FIG. 1B, all of the rotatable strap holders 161, 162, 163, 164 are similarly oriented (e.g. vertically oriented).

Figure 2A:
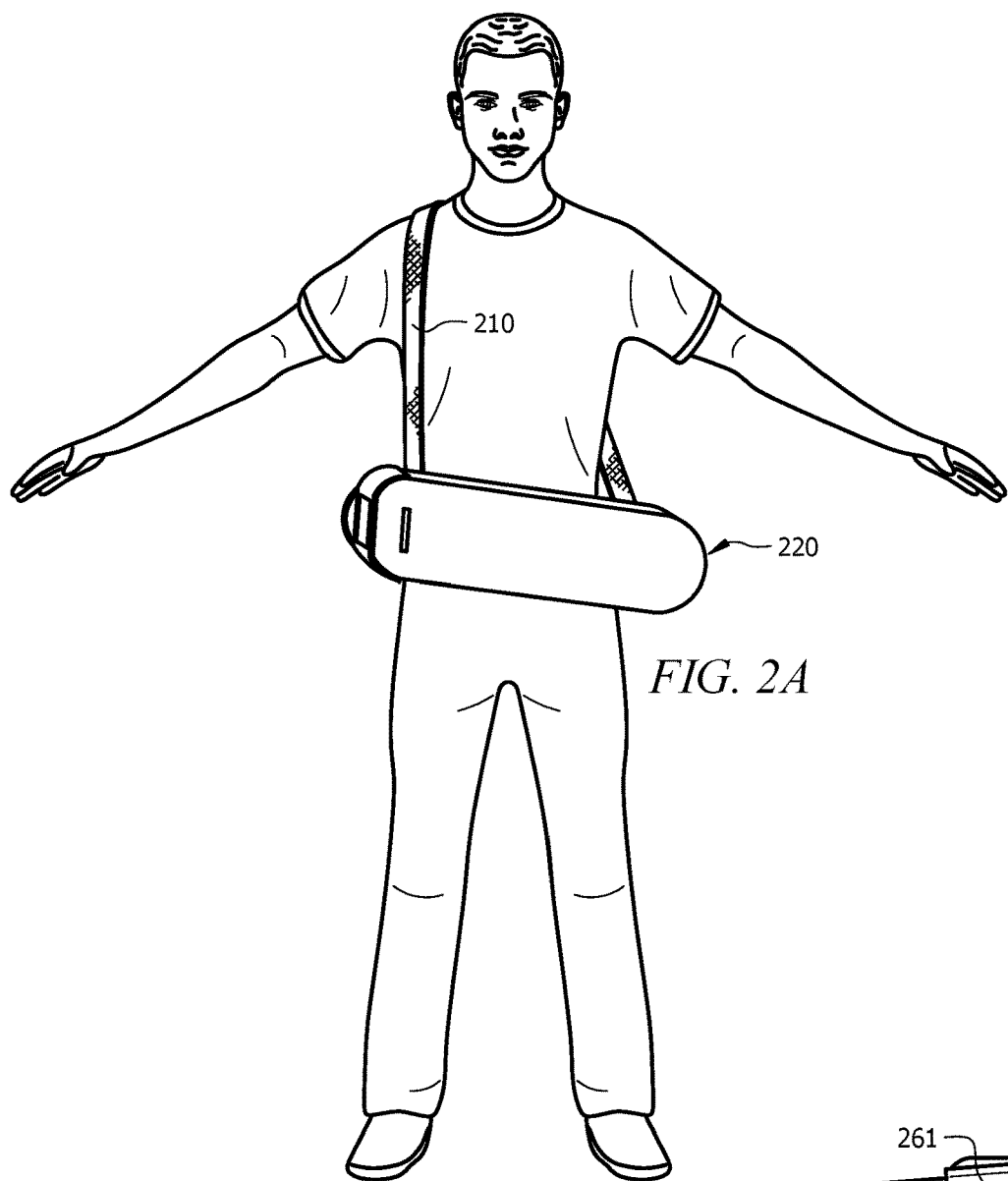
FIG. 2A illustrates a front view of a user wearing an exemplary embodiment of a breathable air system in a waist configuration using a shoulder strap.

FIG. 2A illustrates a front view of a user wearing an exemplary embodiment of a breathable air system 220 in a waist configuration using a shoulder strap 210. The shoulder strap 210 is worn in a similar manner as shown in FIG. 1A (e.g. similar to a messenger bag). However, in the exemplary embodiment of FIG. 2A, the user is shown to have oriented the breathable air system 220 across his waist.

Figure 2B:
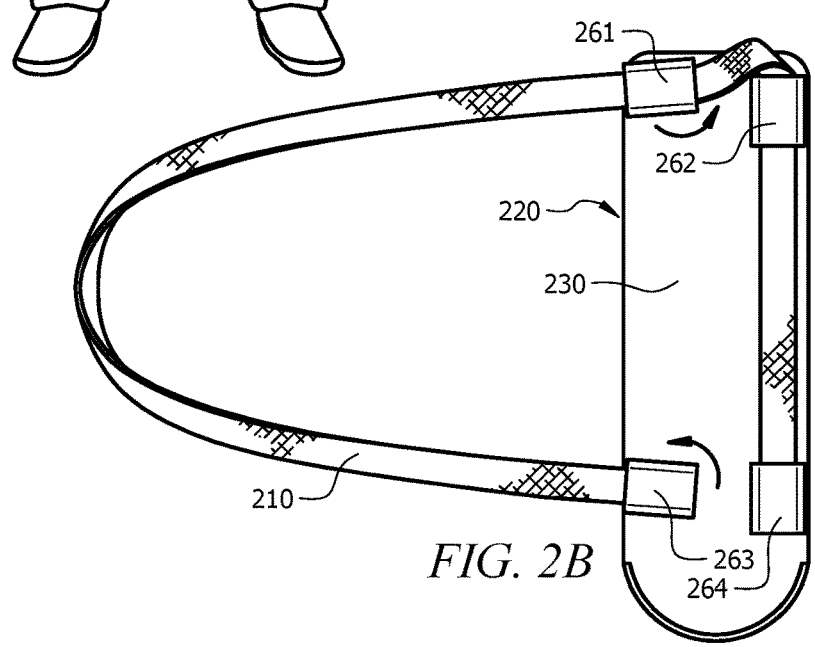
FIG. 2B illustrates a back view of an exemplary embodiment of a breathable air system configured for interaction with a user's waist and comprising a shoulder strap (similar to the exemplary embodiment shown in FIG. 2A)

FIG. 2B illustrates a back view of an exemplary embodiment of a breathable air system 220 configured for interaction with a user's waist and comprising a shoulder strap 210 (similar to the exemplary embodiment shown in FIG. 2A), and shows how to configure the shoulder strap 210 accordingly using the rotatable strap holders 261, 262, 263, 264. Similar to the exemplary embodiment of FIG. 1B, the exemplary embodiment shown in FIG. 2B comprises two attachments 261, 262 located on the upper/top half of the back plate 230 closest to the top of the breathable air system 220, and two attachments 263, 264 located on the lower/bottom half of the back plate 230 closest to the bottom of the breathable air system 220. In the exemplary embodiment of FIG. 2B, the shoulder strap 210 is pulled snugly to the left side of the breathable air system 220 by pulling the shoulder strap 210 located between the top left attachment 261 and the bottom left attachment 263. In this case, the top left attachment 261 and the bottom left attachment 263 are shown to rotate approximately 90 degrees (to allow strap sliding into the configuration). In some embodiments, the shoulder strap 210 may similarly be pulled snugly to the right side of the breathable air system 220 by pulling the shoulder strap 210 located between the top right attachment 262 and the bottom right attachment 264. In this case, the top right attachment 262 and the bottom right attachment 264 would rotate approximately 90 degrees. So, in the configuration of FIG. 2B, the strap holders on each side (e.g. left/right) are similarly oriented, while the strap holders on different sides are oriented at a 90 degree offset. So in FIG. 2B, one of the top strap holders is vertical and one is horizontal, and one of the bottom strap holders is vertical while the other is horizontal (with the strap holders on each side (left/right) oriented similarly).

FIG. 3A illustrates a back view of a user wearing an exemplary embodiment of a breathable air system 320 in a back configuration using two shoulder straps 310a, 310b (although as shown in FIG. 3B, these are actually formed from a single strap via configuration of the rotatable strap holders). In the exemplary embodiment of FIG. 3A, the user is shown to be wearing the breathable air system 320 like a backpack. In other words, one shoulder strap 310a is located on the right shoulder (with the right arm pulled through a loop on the right side of the breathable air system 320), and the other shoulder strap 310b is located on the left shoulder (with the left arm pulled through a loop on the left side of the breathable air system 320).

FIG. 3B illustrates a back view of an exemplary embodiment of a breathable air system 320 configured for interaction with a user's back and comprising two shoulder straps 310a, 310b (similar to the exemplary embodiment shown in FIG. 3A), and shown here to configure the strap accordingly using the rotatable strap holders. In the exemplary embodiment of FIG. 3B, one portion 310b of the shoulder strap 310 is shown to be pulled between the top left attachment 361 and the bottom left attachment 363, and the other portion 310a of the shoulder strap 310 is shown to be pulled between the top right attachment 362 and the bottom right attachment 364. In this manner, two loops (of approximately equal sizes) may be formed on either side of the breathable air system 320 (from the single strap 310 and the configuration of the rotatable strap holders) to serve as two shoulder straps 310a, 310b such that the user may wear the breathable air system 320 in a back configuration. As shown in the exemplary embodiment of FIG. 3B, the rotatable strap holders 360 are shown to be rotated approximately 90 degrees when compared to the rotatable strap holders 160 shown in the exemplary embodiment of FIG. 1B. Thus, in the configuration of FIG. 3B, all of the rotatable strap holders are similarly positioned/oriented horizontally.

FIG. 4A illustrates a perspective view of an exemplary rotatable strap holder 460 comprising a first portion 461 and a second portion 462. Typically, the first portion 461 of the rotatable strap holder 460 may be configured to attach to the back plate of the breathable air system (e.g. using stitching, adhesive, etc.), and the second portion 462 of the rotatable strap holder 460 may interact with the at least one shoulder strap. In the exemplary embodiment of FIG. 4A, the second portion 462 of the rotatable strap holder 460 comprises a first end 462a configured to rotatably attach to the first portion 461 of the rotatable strap holder 460 (e.g. using a snap fit feature, screw feature, etc.) and a second end 462b comprising an aperture/opening 463 to allow insertion of the at least one shoulder strap. In some embodiments, the first portion 461 of the rotatable strap holder 460 may detach from the second portion 462 of the rotatable strap holder 460. In some embodiments, the first portion 461 of the rotatable strap holder 460 may be permanently affixed to the second portion 462 of the rotatable strap holder 460. In this disclosure, "permanently affixed" means that the user would have a difficult time removing the first portion 461 from the second portion 462 and/or may cause the rotatable strap holder 460 to break and/or be damaged by trying to separate the first portion 461 from the second portion 462. For some embodiments of the rotatable strap holder 460, the strap may slide through the aperture/opening 463 (to allow adjustment of the related portion of the strap), while in other embodiments the strap may be fixed (to not slide for example) with regards to the holder (for example, an end of the strap configured to not pass through the aperture/opening). In some embodiments, the plurality of attachments may comprise buckles, hooks, D-rings, carabiners, metal-head buckles, or other attachment mechanisms which allow for easy and secure attachment.

FIG. 4B illustrates a side view of an exemplary embodiment of a rotatable strap holder 460 comprising a first portion 461 and a second portion 462 (similar to the exemplary embodiment shown in FIG. 4A). Generally, the first portion 461 of the rotatable strap holder 460 and the second portion 462 of the rotatable strap holder 460 may interact in a similar manner as discussed above in reference to FIG. 4A. In some embodiments, the shape of the rotatable strap holder 460 may vary. For example, the second end 462b of the second portion 462 of the rotatable strap holder 460 may comprise varying shapes such as a square, rectangle, triangle, circle, rhombus, etc. as long as the second end 462b of the second portion 462 comprises an aperture/opening 463 to allow insertion of the at least one shoulder strap. In some embodiments, the first portion 461 of the rotatable strap holder 460 may comprise varying shapes and sizes (e.g. square, rectangle, triangle, rhombus, etc.), and may comprise different mechanical joints between the first portion 461 of the rotatable strap holder 460 and the second portion 462 of the rotatable strap holder 460 (e.g. ball and socket joint).

Figure 5:
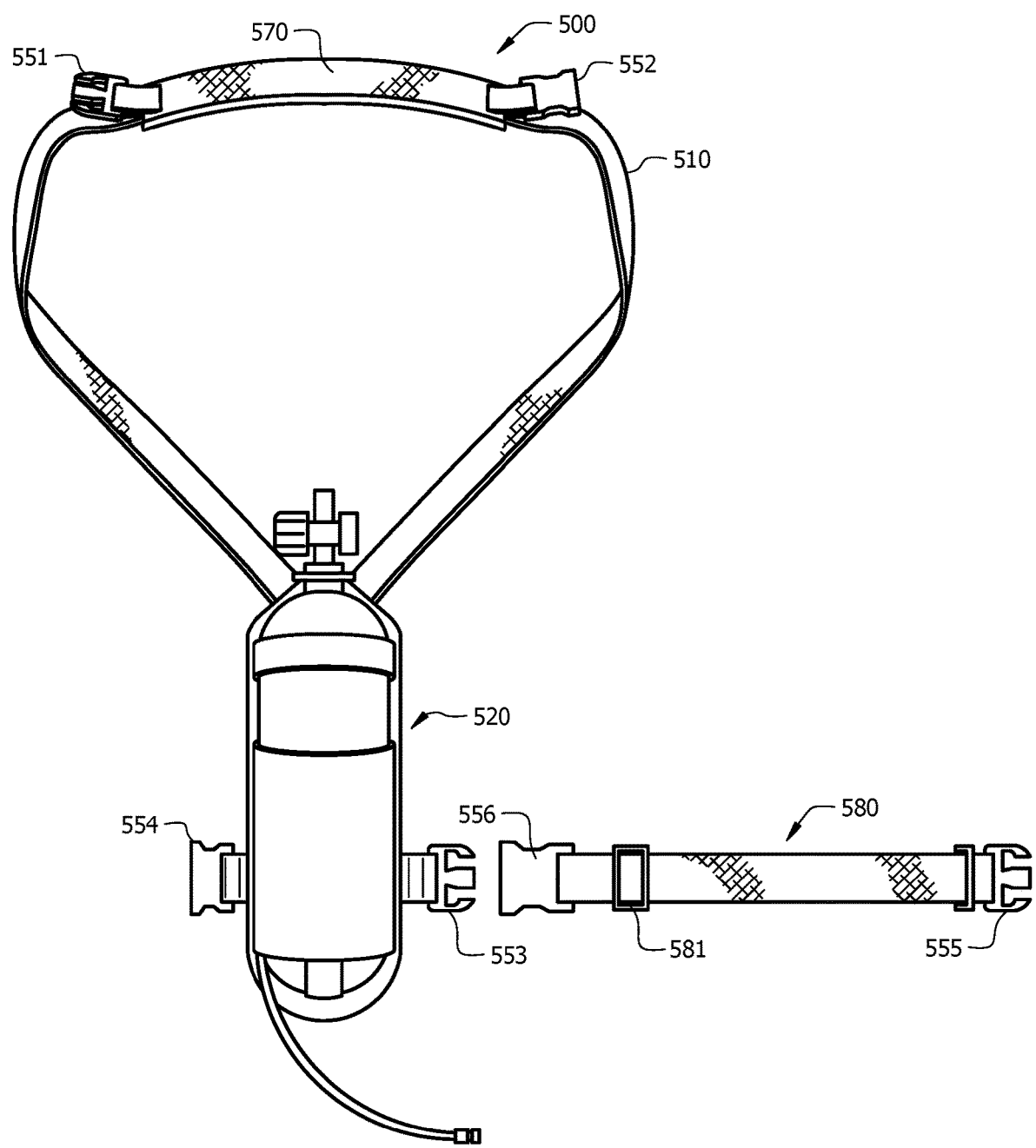
FIG. 5 illustrates a front view of an exemplary embodiment of a breathable air system comprising a shoulder strap and an additional strap configured to attach to the lower half of the breathable air system.

FIG. 5 illustrates a front view of an alternative exemplary embodiment of a breathable air system 520 comprising a shoulder strap 510 and an additional/accessory strap 580 configured to attach to the lower half of the breathable air system 520 (and FIG. 6-FIG. 9B illustrate various configurations for this embodiment). In the exemplary embodiment of FIG. 5, the breathable air system 520 may comprise a gauge, a valve, a hose, and an oxygen tank/cylinder. However, in some embodiments, the breathable air system 520 may comprise additional parts or fewer parts. Generally, the harness design may secure the breathable air system 520 to the harness 500. In the exemplary embodiment of FIG. 5, the harness 500 comprises a shoulder strap 510 (and typically a sleeve or housing configured to hold the cylinder, with the strap attached to such housing, although in other embodiments the strap and attachments might directly mount on the cylinder—it should be understood that any description of attachment to the breathable air system includes indirect attachment within the housing. The shoulder strap 510 is shown to comprise an optional pad 570 configured to interact with the user's shoulders, waist, and/or back (depending on the configuration the user chooses). The shoulder strap 510 is shown to further comprise one or more attachments configured to interact with the other attachments located on the harness 500 and/or the additional/accessory strap 580. Generally, at least one attachment may be located on a first end of the pad 570 (e.g. a male attachment 551 of the shoulder strap 510) and at least one attachment may be located on a second end of the pad 570 (e.g. a female attachment 552 of the shoulder strap 510) (not shown here) (or if there is no pad, then one attachment may be located on the strap between the ends of the strap and at a point approximately halfway between the ends of the strap or the point of attachment to the sleeve for the tank, while the other attachment may similarly be located on the other side of the strap). Additionally, the at least one shoulder strap 510 may comprise a length adjustment mechanism, for example, to better fit varying body types/sizes. In some embodiments, the length adjustment mechanism may comprise one or more strap adjusters, strap loops, and/or clasp buckles.

More specifically, the exemplary embodiment of FIG. 5 comprises four to six attachments 551, 552, 553, 554, 555, 556. The attachments may include a male attachment 551 of the shoulder strap 510, a female attachment 552 of the shoulder strap, a male attachment 553 of the breathable air system 520 (e.g. the sleeve/plate for holding the tank), a female attachment 554 of the breathable air system 520 (e.g. the sleeve/plate for holding the tank), and optionally a male attachment 555 of the additional/accessory strap 580 used in some configurations and not in others, and a female attachment 556 of the additional/accessory strap 580 used in some configurations and not in others. In some embodiments, the number of attachments may vary. For example, some embodiments may comprise two, four, six, eight, ten, twelve, or more attachments. In the exemplary embodiment of FIG. 5, the attachments comprise buckles. In some embodiments, the attachments may vary and may comprise rotatable strap holders, hooks, D-rings, carabiners, metalhead buckles, or other attachment mechanisms which allow for easy and secure attachment.

Figure 6:
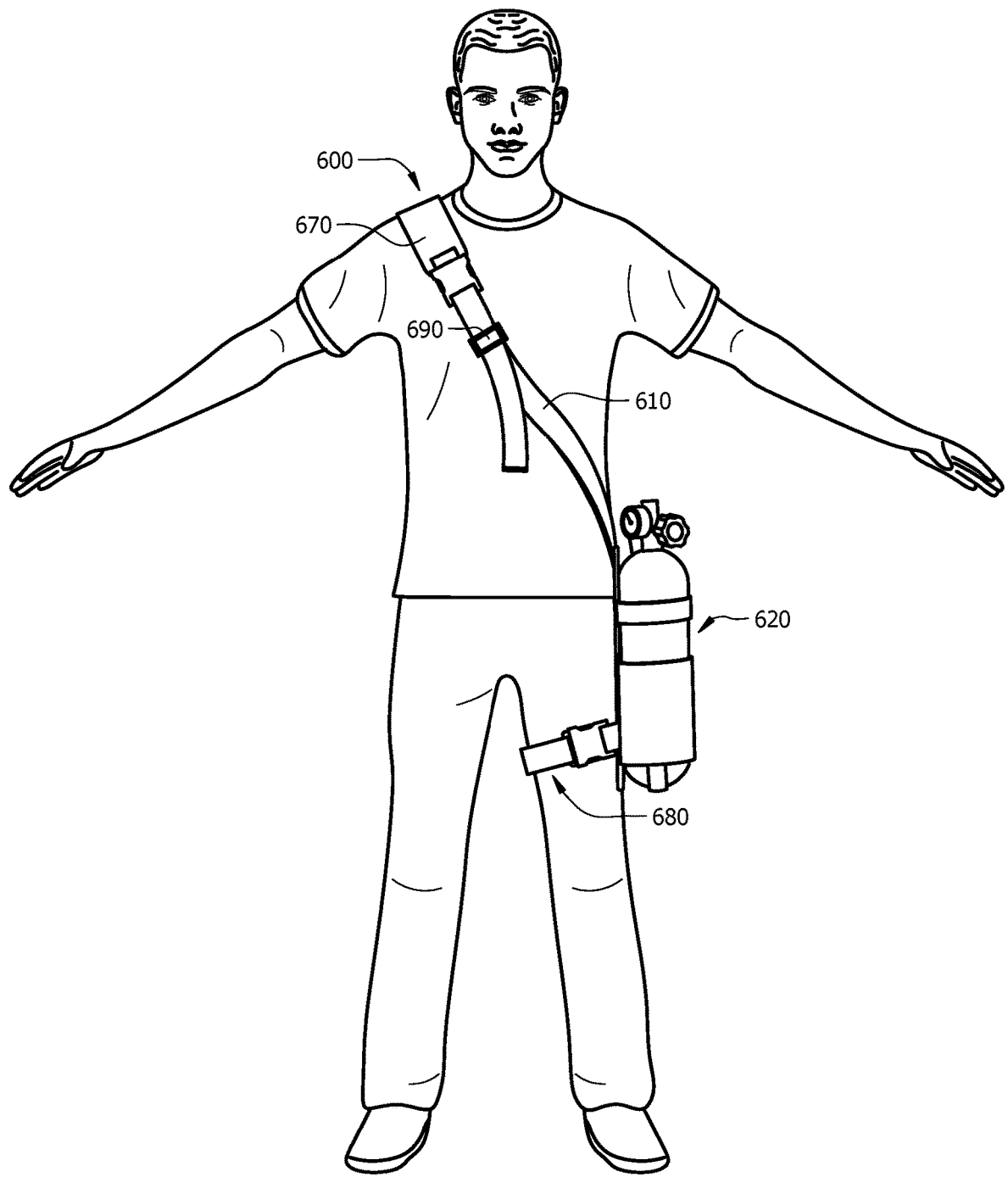
FIG. 6 illustrates a front view of a user wearing an exemplary embodiment of a breathable air system comprising a shoulder strap and an additional strap.

FIG. 6 illustrates a front view of a user wearing an exemplary embodiment of a breathable air system 620 comprising a shoulder strap 610 and an additional/accessory strap 680. In the exemplary embodiment of FIG. 6, the user is shown to have configured the breathable air system 620 on the side of his body such that the breathable air system 620 interfaces with his hip and leg. The harness 600 shown in FIG. 6 comprises a shoulder strap 610 with a length adjustment mechanism 690 attached to the upper half of the breathable air system 620. The harness 600 shown in FIG. 6 also comprises an additional/accessory strap 680 to secure the lower half of the breathable air system 620 to his leg. In the exemplary embodiment of FIG. 6, the user is shown to be wearing the breathable air system 620 on his left side. However, in some embodiments, the user may wear the breathable air system 620 on the right side of the body with a similar harness configuration.

To obtain the exemplary configuration shown in FIG. 6 from the exemplary configuration shown in FIG. 5, the user may place the shoulder strap 610 comprising the pad 670 on his/her shoulder (with the strap hanging across the user's body). The user may then adjust the breathable air system 620 to interface with the side of the body opposite the shoulder (e.g. if the user places the shoulder strap 610 on the right shoulder, then the user may place the breathable air system 620 such that it interfaces with the left side of the body (in a cross-body style)). To further secure the additional/accessory strap 680 around his/her leg, the user may (optionally) attach the male attachment 555 of the additional/accessory strap 580 to the female attachment 554 of the breathable air system 520, and the user may attach the female attachment 556 of the additional/accessory strap 580 to the male attachment 553 of the breathable air system 520. To securely tighten the additional/accessory strap 680 around the user's leg, the user may adjust the adjustment mechanism 581 located on the additional/accessory strap 680 until the additional/accessory strap 680 is wrapped snugly around the user's leg.

Figure 7A:
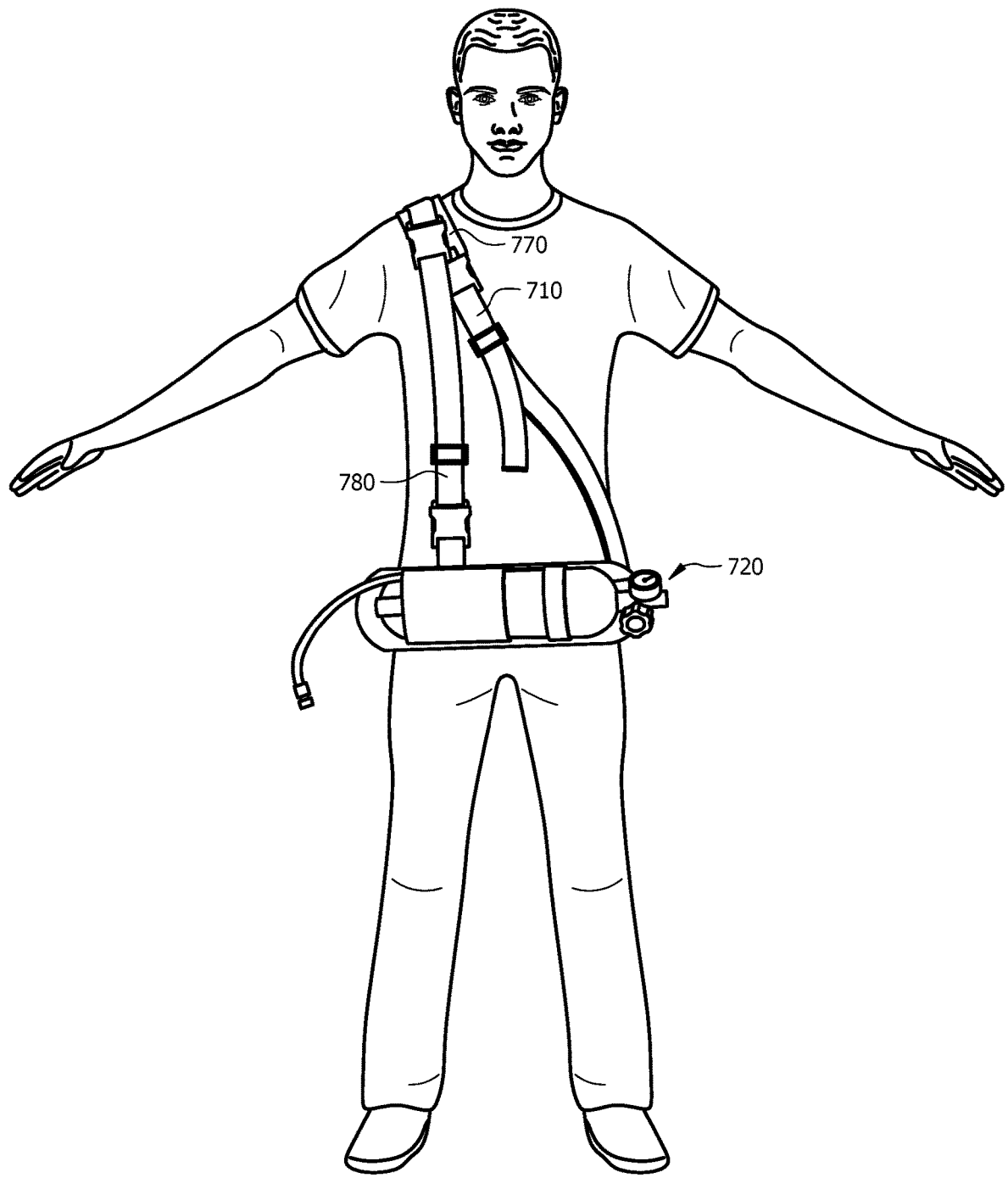
FIG. 7A illustrates a front view of a user wearing an exemplary embodiment of a breathable air system in a waist configuration comprising a shoulder strap and an additional strap.

FIG. 7A illustrates a front view of a user wearing an exemplary embodiment of a breathable air system 720 in a waist configuration comprising a shoulder strap 710 and an additional/accessory strap 780. In the exemplary embodiment of FIG. 7A, the user is shown to have adjusted the breathable air system 720 to lie across his waist. To obtain the exemplary configuration shown in FIG. 7A from the exemplary configuration shown in FIG. 5, the user may place the shoulder strap 710 comprising the pad 770 on his/her shoulder. The user may then adjust the breathable air system 720 to interface with his/her waist such that the upper/top part of the breathable air system 720 is closest to the opposite side of the body from the shoulder with which the shoulder strap 710 is interfacing. In other words, the shoulder strap 710 is shown to have a cross-body configuration. To maintain the breathable air system 720 in a horizontal position across the user's waist, the user may use the additional/accessory strap 780. In the exemplary embodiment of FIG. 7A, the additional/accessory strap 780 is shown to attach to the lower/bottom half of the breathable air system 720 and to the shoulder strap 710 (the shoulder strap 710 is shown to comprise two attachments on the front side of the shoulder pad 770). In this manner, the additional/accessory strap 780 is configured to interact with the front of the user's body and not the back of the user's body. Typically, this may be accomplished by attaching the male attachment 555 of the additional/accessory strap 580 to the female attachment 552 of the shoulder strap 570 and by attaching the female attachment 556 of the additional/accessory strap 580 to the male attachment 553 of the breathable air system 520. In some embodiments, the additional/accessory strap 780 may attach to the lower/bottom half of the breathable air system 720 and may interface with the same shoulder as the shoulder strap 710. In this manner, the additional/accessory strap 780 may lie substantially vertically across the user's body as shown in FIG. 7A and may interact with both the front and the back of the user's body. Typically, this may be accomplished by attaching the male attachment 555 of the additional/accessory strap 580 to the female attachment 554 of the breathable air system 520 and by attaching the female attachment 556 of the additional/accessory strap 580 to the male attachment 553 of the breathable air system 520, and then adjusting the length of the additional/accessory strap 580 (and/or the shoulder strap 570) to position and orient the breathable air system into a substantially horizontal configuration. Persons of skill will understand that alternatively the configuration shown in FIG. 7A could be worn on the user's opposite shoulder.

Figure 7B:
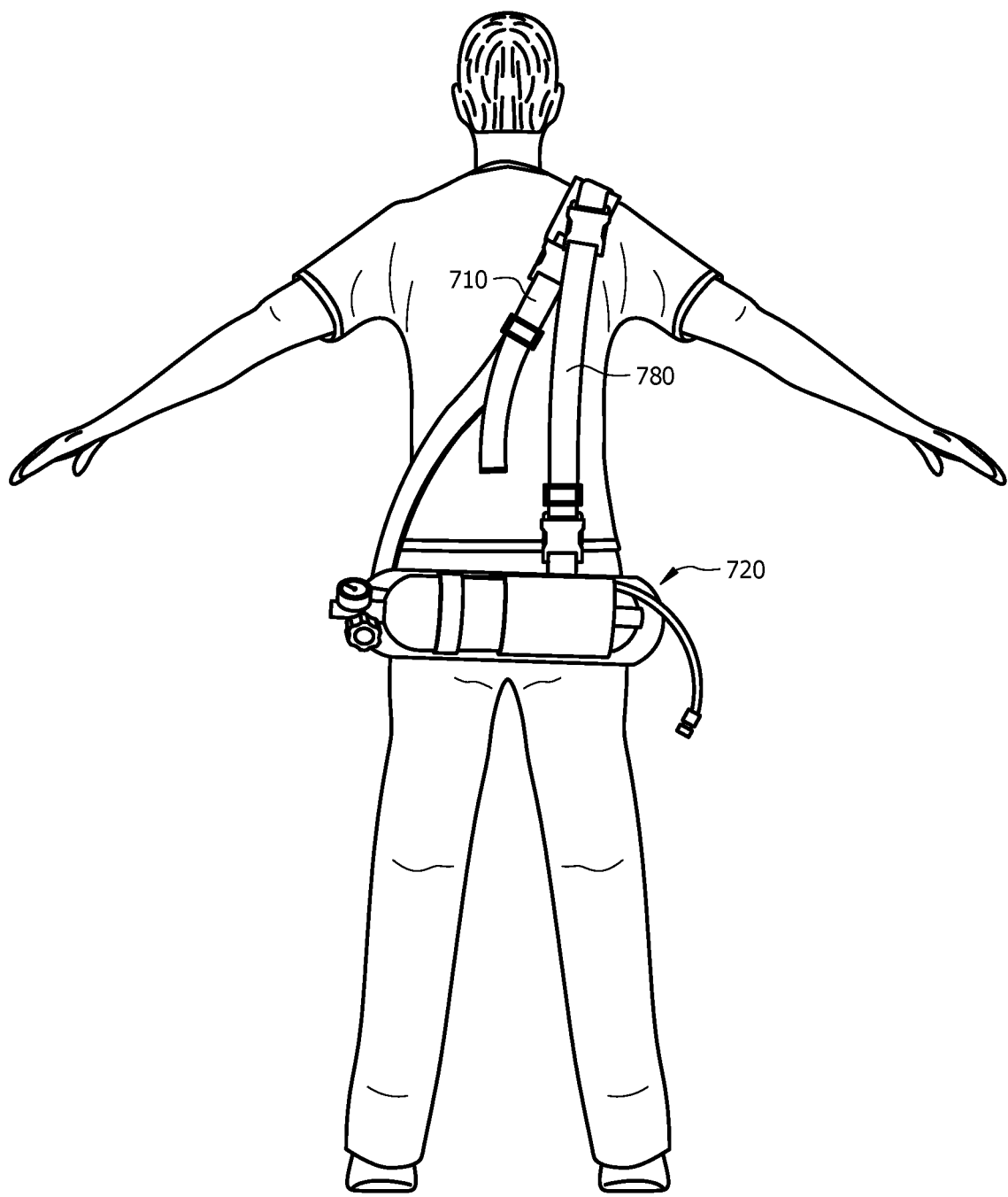
FIG. 7B illustrates a back view of a user wearing an exemplary embodiment of a breathable air system in a lower back configuration comprising a shoulder strap and an additional strap (similar to the exemplary embodiment shown in FIG. 7A)

FIG. 7B illustrates a similar configuration worn with the breathable air system on the user's back side. So, FIG. 7B shows a back view of a user wearing an exemplary embodiment of a breathable air system 720 in a lower back configuration comprising a shoulder strap 710 and an additional/accessory strap 780 (similar to the exemplary embodiment shown in FIG. 7A). In the exemplary embodiment of FIG. 7B, the breathable air system 720 is shown to be oriented in a similar manner as the exemplary embodiment in FIG. 7A on the backside of the user's body rather than the front side. In the exemplary embodiment of FIG. 7B, the shoulder strap 710 is shown to have a cross-body configuration. In other words, the shoulder strap 710 is shown to extend from the user's right shoulder to the user's left side of the body. In the exemplary embodiment of FIG. 7B, the breathable air system 720 is shown to be placed horizontally across the back side of the user's body (e.g. in proximity to the user's lower back). To support the lower/bottom half of the breathable air system 720 in a horizontal configuration, an additional/accessory strap 780 is shown to be attached to the attachments on the lower/bottom half of the breathable air system 720 to the attachment on the shoulder strap. Typically, this may be accomplished by attaching the male attachment 555 of the additional/accessory strap 580 to the female attachment 556 of the breathable air system 520 and by attaching the female attachment 554 of the additional/accessory strap 580 to the male attachment 551 of the shoulder strap 510. In some embodiments, this may be accomplished by attaching the male attachment 555 of the additional/accessory strap 580 to the female attachment 554 of the breathable air system 520 and by attaching the female attachment 556 of the additional/accessory strap 580 to the male attachment 553 of the breathable air system 520. The length(s) of the straps can then be adjusted for substantially horizontal orientation of the tank. Persons of skill will appreciate that alternatively the configuration of FIG. 7B can be worn on the opposite shoulder.

Figure 8:
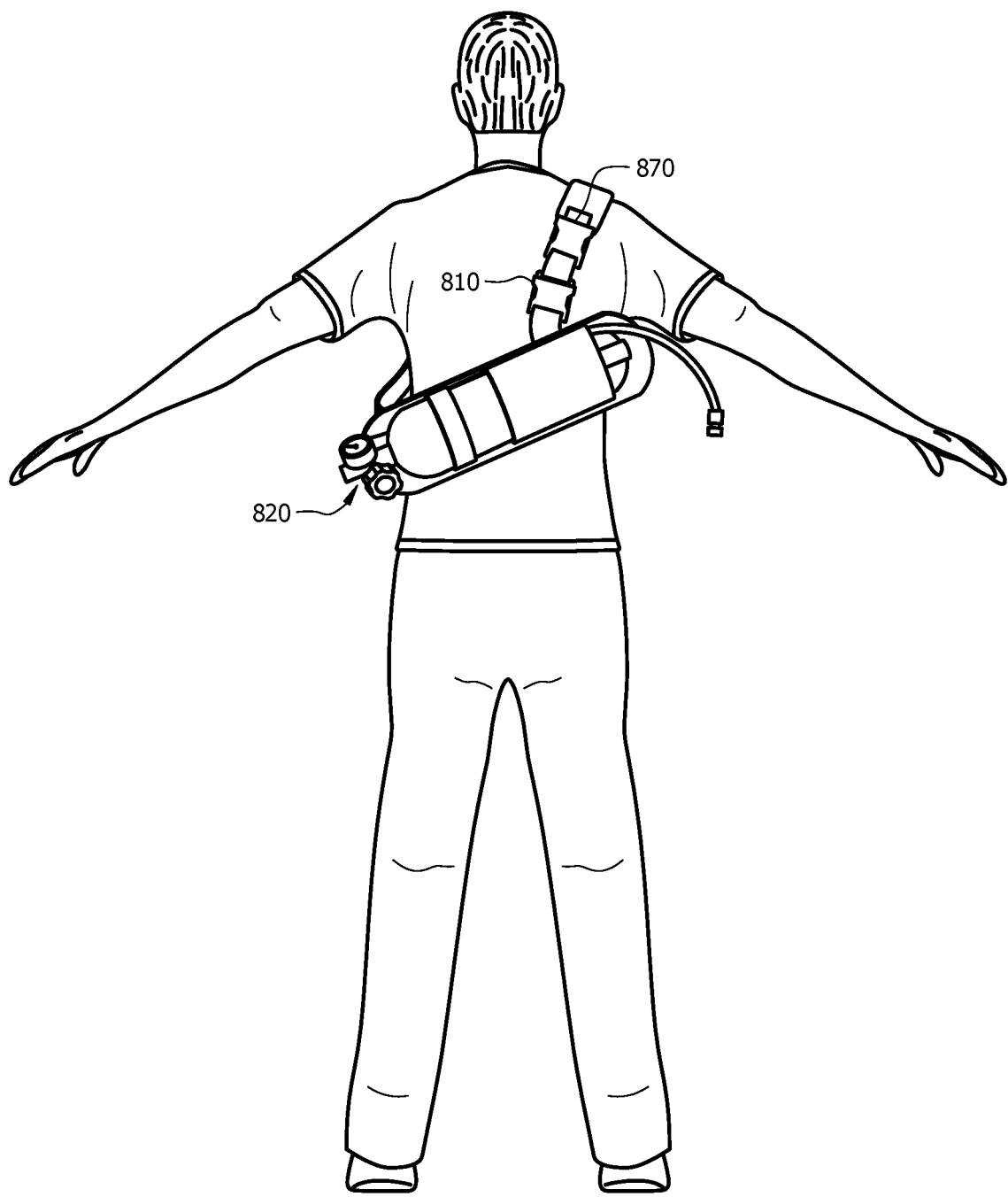
FIG. 8 illustrates a back view of a user wearing an exemplary embodiment of a breathable air system in a back configuration comprising a shoulder strap.

FIG. 8 illustrates a back view of a user wearing an exemplary embodiment of a breathable air system 820 in a back configuration comprising a shoulder strap 810. In the exemplary embodiment of FIG. 8, the breathable air system 820 is configured to interface with the upper to middle back area of the user (with the strap worn across the body). To obtain the exemplary configuration shown in FIG. 8 from the exemplary configuration shown in FIG. 5, the user may insert the male attachment 553 of the breathable air system into the female attachment 552 of the shoulder strap 510 (and optionally adjust its length). The user may then insert his/her head and arm through the larger loop formed such that the pad 870 located on the shoulder strap 810 interfaces with his/her shoulder (e.g. the shoulder opposite the arm inserted through the larger loop).

Figure 9A:
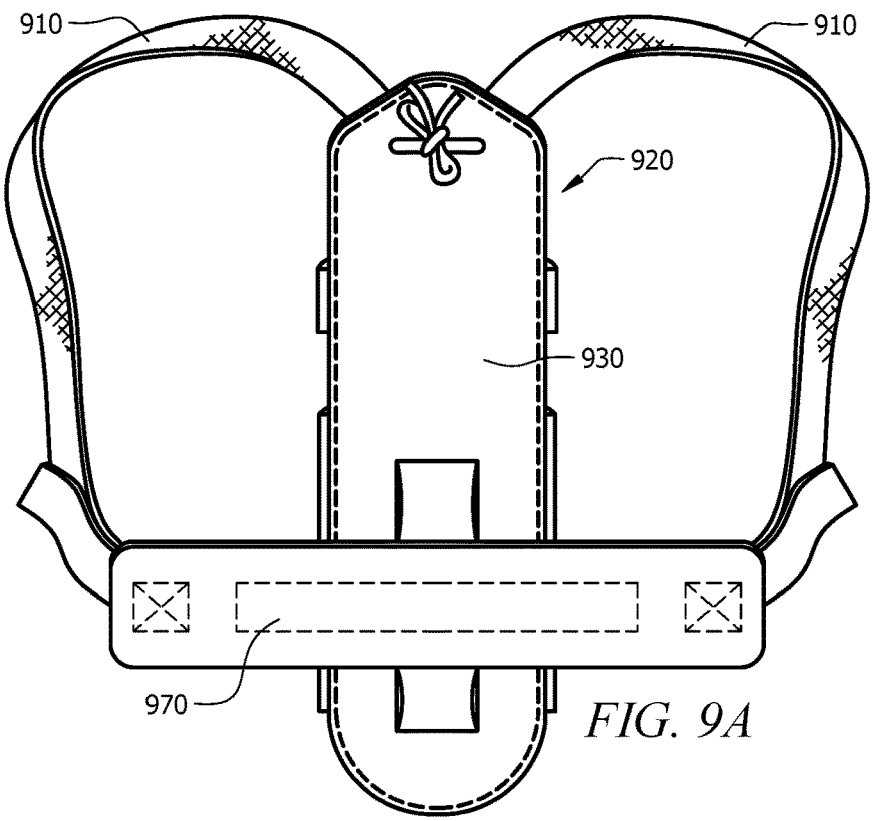
FIG. 9A illustrates a front view of an exemplary embodiment of a breathable air system comprising two shoulder straps and a pad.

FIG. 9A illustrates a front view of an exemplary embodiment of a breathable air system 920 configured (as a backpack) to have two shoulder straps 910 and a pad 970. In the exemplary embodiment of FIG. 9A, the breathable air system 920 is configured to be worn on a user's back (for example, like a backpack). To obtain the exemplary configuration shown in FIG. 9A from the exemplary configuration shown in FIG. 5, the user may insert the male attachment 553 of the breathable air system 520 into the female attachment 552 of the shoulder strap 510, and the user may insert the male attachment 551 of the shoulder strap 510 into the female attachment 554 of the breathable air system 520. The strap/loop length may then be optionally adjusted for user comfort. In this manner, the pad 970 located on the at least one shoulder strap 910 may be located on the lower/bottom half of the breathable air system 920. Additionally, the pad 970 may lay adjacent to or may interface with the back plate 930 of the breathable air system 920. In the exemplary configuration shown in FIG. 9A, the two loops 910a and 910b formed on both sides of the breathable air system 920 allow the user to insert his/her arms such that the pad 970 and the back plate 930 of the breathable air system 920 interface with the user's back.

Figure 9B:
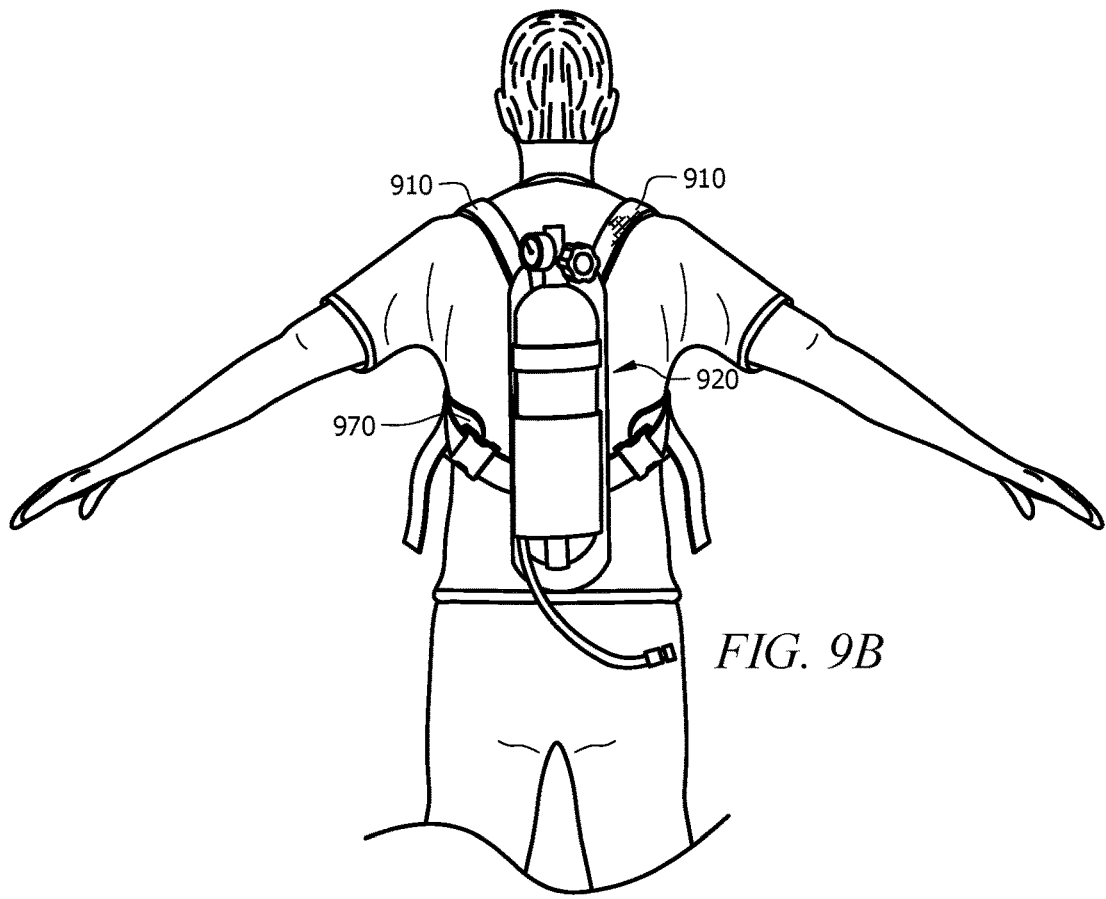
FIG. 9B illustrates a back view of a user wearing an exemplary embodiment of a breathable air system in a back configuration comprising two shoulder straps and a pad (similar to the exemplary embodiment shown in FIG. 9A).

FIG. 9B illustrates a back view of a user wearing an exemplary embodiment of a breathable air system 920 in a back configuration comprising two shoulder straps 910 and a pad 970 (similar to the exemplary embodiment shown in FIG. 9A). In the exemplary embodiment of FIG. 9B, the breathable air system 920 is shown to be worn in a backpack configuration. Generally, the breathable air system 920 may lie approximately vertically across the user's back as shown in the exemplary embodiment of FIG. 9B. As shown, the pad 970 interfaces with the user's back to provide for an increased level of comfort. Additionally, the two shoulder straps 910 may be adjusted to fit the user's preferences.

Having described device embodiments above, especially with regard to the figures, various additional embodiments can include, but are not limited to the following:

In a first embodiment, a harness for carrying (at least a portion of) a breathable air system, wherein the harness comprises: at least one shoulder strap; and a plurality of attachment mechanisms configured to attach the at least one shoulder strap to the breathable air system, and configured to orient the at least one shoulder strap into one of a plurality of strap configurations. A second embodiment may include the harness of the first embodiment, wherein the plurality of strap configurations (typically removably) comprise (positioning the breathable air system on) one or more of the hip, waist, leg, and back of a user. A third embodiment may include the harness of the first to second embodiments, wherein the plurality of attachments comprise buckles, hooks, D-rings, carabiners, or rotatable strap holders, wherein the rotatable strap holders are configured to allow the at least one shoulder strap to slide and rotate 360 degrees. A fourth embodiment may include the harness of the first to third embodiments, wherein the breathable air system further comprises a back plate, wherein when the harness is positioned into one of a plurality of strap configurations, the back plate interfaces with the user. A fifth embodiment may include the harness of the first to fourth embodiments, wherein the rotatable strap holder comprises a first portion configured to attach to the back plate of the breathable air system and a second portion configured to interact with the at least one shoulder strap. A sixth embodiment may include the harness of the first to fifth embodiments, wherein the first portion of the rotatable strap holder is configured to detach from the second portion of the rotatable strap holder. A seventh embodiment may include the harness of the first to sixth embodiments, wherein the second portion of the rotatable strap holder comprises a first end configured to rotatably attach to the first portion of the rotatable strap holder and a second end comprising an aperture/opening to allow insertion of the at least one shoulder strap. An eighth embodiment may include the harness of the first to seventh embodiments, further comprising at least one additional/accessory strap, wherein the at least one additional/accessory strap is configured to attach to at least one of a plurality of attachments located on the breathable air system, the at least one shoulder strap, or both. A ninth embodiment may include the harness of the first to eighth embodiments, wherein the at least one shoulder strap further comprises at least one of a pad configured to interact with the user's shoulders or waist and a length adjustment mechanism, wherein the length adjustment mechanism comprises one or more strap adjusters, strap loops, or clasp buckles. A tenth embodiment may include the harness of the first to ninth embodiments, wherein at least two attachments are attached to the top half of the back plate and at least two attachments are attached to the bottom half of the back plate. An eleventh embodiment may include the harness of the first to tenth embodiments, wherein a first attachment is configured to secure one end of the at least one shoulder strap to the (bottom half of the) back plate, a second attachment is configured to secure the opposite end of the at least one shoulder strap to the (bottom half of the) back plate (adjacent to the first attachment), and a third attachment is configured to secure the portion of the at least one shoulder strap located between the first attachment and the second attachment to the (top half of the) back plate. A twelfth embodiment may include the harness of the first to eleventh embodiments, wherein the first strap configuration comprises positioning the breathable air system on the user's hip, wherein the at least one shoulder strap is pulled snugly through the at least two attachments located on the top half of the back plate, thereby forming a loop above the breathable air system for interaction with the user's shoulders. A thirteenth embodiment may include the harness of the first to twelfth embodiments, wherein the second strap configuration comprises positioning the breathable air system on the user's waist, wherein the at least one shoulder strap is pulled snugly to the same (either the left/first or the right/second) side through the at least two attachments located on the top half of the back plate and the at least two attachments located on the bottom half of the back plate. A fourteenth embodiment may include the harness of the first to thirteenth embodiments, wherein the third strap configuration comprises positioning the breathable air system on the user's back, (wherein the at least one shoulder strap is pulled snugly between the at least two attachments located on the top half of the back plate, and) wherein the amount of the at least one shoulder strap pulled to the first side of the breathable air system is approximately equal to the amount of the at least one shoulder strap pulled to the second side of the breathable air system. A fifteenth embodiment may include the harness of the first to fourteenth embodiments, wherein the at least one of a pad comprises at least two attachments, wherein the first attachment is located on a first end of the pad, wherein the second attachment is located on a second end of the pad. A sixteenth embodiment may include the harness of the first to fifteenth embodiments, wherein at least two attachments are located on the bottom half of the breathable air system, and wherein the at least two attachments located on the bottom half of the breathable air system are configured to interact with the at least two attachments located on the at least one of a pad. A seventeenth embodiment may include the harness of the first to sixteenth embodiments, wherein the harness comprises a bag and/or cylinder and/or hose and other elements required by the breathable air system.

Exemplary embodiments might also relate to a method for adjusting wearing configurations of a harness used for carrying (at least a portion of) a breathable air system (e.g. similar to those described above, which may be considered optionally incorporated herein with respect to the discussion of the system). Such method embodiments, for example, might include, but are not limited to, the following:

In an eighteenth embodiment, a method for adjusting wearing configurations of a harness used for carrying (at least a portion of) a breathable air system, the method comprising two or more of the following: configuring the harness to a horizontal wearing configuration; configuring the harness to a back wearing configuration; and configuring the harness to a hip wearing configuration. A nineteenth embodiment may include the method of the eighteenth embodiment, wherein configuring the harness to a horizontal wearing configuration comprises connecting a male attachment of an additional/accessory strap to a female attachment of a shoulder strap and connecting a female attachment of the additional/accessory strap to a male attachment of the breathable air system, (or wherein configuring the harness to a horizontal wearing configuration comprises connecting a female attachment of an additional/accessory strap to a male attachment of a shoulder strap and connecting a male attachment of the additional/accessory strap to a female attachment of the breathable air system). A twentieth embodiment may include the method of the eighteenth to the nineteenth embodiments, further comprising: repositioning/orienting the harness to the front of the user's body or the back of the user's body; adjusting the length of the shoulder strap, the additional/accessory strap, or both the shoulder strap and the additional/accessory strap; and adjusting the harness for user comfort and fit. A twenty-first embodiment may include the method of the eighteenth to the twentieth embodiments, wherein configuring the harness to a hip wearing configuration from the horizontal wearing configuration comprises: disconnecting the male attachment of the additional/accessory strap from the female attachment of the shoulder strap (or disconnecting the female attachment of the additional/accessory strap from the male attachment of the shoulder strap). A twenty-second embodiment may include the method of the eighteenth to twenty-first embodiments, wherein configuring the harness to a back wearing configuration from the horizontal wearing configuration comprises: disconnecting the male attachment of the additional/accessory strap from the female attachment of the shoulder strap (or disconnecting the female attachment of the additional/accessory strap from the male attachment of the shoulder strap); and disconnecting the female attachment of the additional/accessory strap from the male attachment of the breathable air system (or disconnecting the male attachment of the additional/accessory strap from the female attachment of the shoulder strap). A twenty-third embodiment may include the method of the eighteenth to twenty-second embodiments, wherein configuring the harness to a hip wearing configuration comprises: orienting a shoulder strap over the user's shoulder; adjusting the length of the shoulder strap; and adjusting the harness for user comfort and fit. A twenty-fourth embodiment may include the method of the eighteenth to twenty-third embodiments, further comprising attaching an additional/accessory strap around the user's leg, wherein attaching the additional/accessory strap comprises: connecting a male attachment of the additional/accessory strap to a female attachment of a breathable air system; wrapping the additional/accessory strap around the user's leg; and connecting a female attachment of the additional/accessory strap to a male attachment of the breathable air system. A twenty-fifth embodiment may include the method of the eighteenth to twenty-fourth embodiments, wherein configuring the harness to a back wearing configuration comprises: connecting a female attachment of a shoulder strap to a male attachment of a breathable air system; and connecting a male attachment of the shoulder strap to the female attachment of the breathable air system. A twenty-sixth embodiment may include the method of the eighteenth to twenty-fifth embodiments, further comprising: orienting the breathable air system on the user's back; positioning the shoulder straps on the user's shoulders; adjusting the length of the shoulder straps; and adjusting the harness for user comfort and fit.

While various embodiments in accordance with the principles disclosed herein have been shown and described above, modifications thereof may be made by one skilled in the art without departing from the spirit and the teachings of the disclosure. The embodiments described herein are representative only and are not intended to be limiting. Many variations, combinations, and modifications are possible and are within the scope of the disclosure. Alternative embodiments that result from combining, integrating, and/or omitting features of the embodiment(s) are also within the scope of the disclosure. Accordingly, the scope of protection is not limited by the description set out above, but is defined by the claims which follow that scope including all equivalents of the subject matter of the claims. Each and every claim is incorporated as further disclosure into the specification, and the claims are embodiment(s) of the present invention(s). Furthermore, any advantages and features described above may relate to specific embodiments, but shall not limit the application of such issued claims to processes and structures accomplishing any or all of the above advantages or having any or all of the above features.

Additionally, the section headings used herein are provided for consistency with the suggestions under 37 C.F.R. 1.77 or to otherwise provide organizational cues. These headings shall not limit or characterize the invention(s) set out in any claims that may issue from this disclosure. Specifically and by way of example, although the headings might refer to a "Field," the claims should not be limited by the language chosen under this heading to describe the so-called field. Further, a description of a technology in the "Background" is not to be construed as an admission that certain technology is prior art to any invention(s) in this disclosure. Neither is the "Summary" to be considered as a limiting characterization of the invention(s) set forth in issued claims. Furthermore, any reference in this disclosure to "invention" in the singular should not be used to argue that there is only a single point of novelty in this disclosure. Multiple inventions may be set forth according to the limitations of the multiple claims issuing from this disclosure, and such claims accordingly define the invention(s), and their equivalents, that are protected thereby. In all instances, the scope of the claims shall be considered on their own merits in light of this disclosure, but should not be constrained by the headings set forth herein.

Use of broader terms such as "comprises," "includes," and "having" should be understood to provide support for narrower terms such as "consisting of," "consisting essentially of," and "comprised substantially of." Use of the terms "optionally," "may," "might," "possibly," and the like with respect to any element of an embodiment means that the element is not required, or alternatively, the element is required, both alternatives being within the scope of the embodiment(s). Also, references to examples are merely provided for illustrative purposes, and are not intended to be exclusive.

While several embodiments have been provided in the present disclosure, it should be understood that the disclosed systems and methods may be embodied in many other specific forms without departing from the spirit or scope of the present disclosure. The present examples are to be considered as illustrative and not restrictive, and the intention is not to be limited to the details given herein. For example, the various elements or components may be combined or integrated in another system, or certain features may be omitted or not implemented.

Also, techniques, systems, subsystems, and methods described and illustrated in the various embodiments as discrete or separate may be combined or integrated with other systems, modules, techniques, or methods without departing from the scope of the present disclosure. Other items shown or discussed as directly coupled or communicating with each other may be indirectly coupled or communicating through some interface, device, or intermediate component, whether electrically, mechanically, or otherwise. Other examples of changes, substitutions, and alterations are ascertainable by one skilled in the art and could be made without departing from the spirit and scope disclosed herein.

What is claimed is:

1. A harness for carrying a breathable air system, wherein the harness comprises:
   a single shoulder strap; and
   at least four rotatable strap holders configured to attach the single shoulder strap to the breathable air system, and configured to orient the single shoulder strap into a plurality of strap configurations, wherein the plurality of strap configurations comprises one or more of a hip configuration, a waist configuration, and a back configuration;
   wherein each of the at least four rotatable strap holders includes a first portion and a second portion, the first portion configured to be attached to a back plate of the breathable air system, the second portion being rotatably attached to the first portion and defining an aperture extending therethrough to receive the single shoulder strap, wherein an axis of rotation of the second portion is configured to be perpendicular to a surface of the back plate, and the axis of rotation of the second portion is intersects and is perpendicular to a longitudinal axis of the second portion, wherein the aperture extends along the longitudinal axis of the second portion; and
   wherein each of the at least four rotatable strap holders allow rotation of the second portion about a connection of the second portion to the first portion by at least 90 degrees, wherein two of the at least four rotatable strap holders are configured to allow the single shoulder strap to slide with respect to the two rotatable strap holders.

2. The harness of claim 1, wherein the plurality of strap configurations are configured to position the breathable air system on one or more of a hip, a waist, a leg, and a back of a user.

3. The harness of claim 1, wherein two of the at least four rotatable strap holders are attached to to ends of the single shoulder strap to not allow the single shoulder strap to slide therethrough.

4. The harness of claim 1, wherein the at least four rotatable strap holders allow rotation of the second portion about the connection from 180 to 360 degrees.

5. The harness of claim 1, wherein a first rotatable strap holder of the at least four rotatable strap holders is configured to secure one end of the single shoulder strap to a bottom left of the back plate, a second rotatable strap holder of the at least four rotatable strap holders is configured to secure an opposite end of the single shoulder strap to a bottom right of the back plate, a third rotatable strap holder of the at least four rotatable strap holders is configured to secure the single shoulder strap to a top left of the back plate, and a fourth rotatable strap holder of the at least four rotatable strap holders is configured to secure the single shoulder strap to a top right of the back plate.

6. The harness of claim 1, wherein the plurality of strap configurations comprises a first strap configuration, wherein the first strap configuration is the hip configuration, wherein the first strap configuration is configured to position the breathable air system on a hip of a user, wherein the harness is configured such that in the first strap configuration the single shoulder strap is pulled snugly through the two of the at least four rotatable strap holders located on a top half of the back plate, thereby forming a loop above the breathable air system configured for interaction with a shoulder of the user.

7. The harness of claim 1, wherein the plurality of strap configurations comprises a second strap configuration, and wherein the second strap configuration is the waist configuration;
   wherein the at least four rotatable strap holders are configured to be located at least on a top left, a bottom left, a top right, and a bottom right of the back plate; and
   wherein the harness is configured such that in the second strap configuration the single shoulder strap is pulled through either the rotatable strap holders located on the top left and the bottom left of the back plate or the rotatable strap holders located on the top right and the bottom right of the back plate.

8. The harness of claim 1, wherein the plurality of strap configurations comprises a third strap configuration, wherein the third strap configuration is the back configuration, wherein the third strap configuration is configured to position the breathable air system on a back of a user, wherein the harness is configured such that in the third strap configuration an amount of the single shoulder strap pulled to a left side of the breathable air system is equal to an amount of the single shoulder strap pulled to a right side of the breathable air system.

* * * * *